United States Patent [19]

Brown

[11] Patent Number: 5,746,779
[45] Date of Patent: May 5, 1998

[54] QUATERNIZED BLUE ANTHRAQINONE HAIR DYES IN AN ISATIN/AMINE DYE SYSTEM

[75] Inventor: Keith Brown, New Canaan, Conn.

[73] Assignee: Bristol-Myers Squibb Company, New York, N.Y.

[21] Appl. No.: 678,803

[22] Filed: Jul. 12, 1996

[51] Int. Cl.$^6$ .................................. A61K 7/13
[52] U.S. Cl. .................. 8/426; 8/405; 8/407; 8/409; 8/423; 8/606; 8/657; 8/675
[58] Field of Search .................... 8/405, 407, 409, 8/423, 426, 606, 657, 675

[56] References Cited

U.S. PATENT DOCUMENTS

| | | | |
|---|---|---|---|
| 4,750,908 | 6/1988 | Rosenbaum et al. | 8/405 |
| 4,921,503 | 5/1990 | Anderson et al. | 8/405 |
| 5,261,926 | 11/1993 | Lang et al. | 8/409 |
| 5,279,616 | 1/1994 | Lang et al. | 8/406 |
| 5,340,366 | 8/1994 | Lang et al. | 8/409 |
| 5,520,707 | 5/1996 | Lim et al. | 8/426 |

*Primary Examiner*—Paul Lieberman
*Assistant Examiner*—Caroline L. Dusheck
*Attorney, Agent, or Firm*—Morton S. Simon

[57] ABSTRACT

Quaternized blue anthraquinone compounds of Formula I

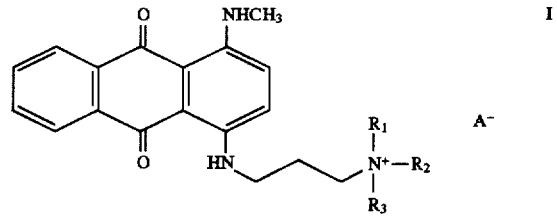

wherein $R_1$ and $R_2$ are methyl and $R_3$ is propyl, or $R_1$ and $R_2$ are ethyl and $R_3$ is methyl and $A^-$ is a cosmetically acceptable anion, when employed in an isatin/amine dye system for the dyeing of hair enable the hair colorist to develop a full range of shades for the isatin/amine dye system. The compound of Formula I wherein R1 and R2 are methyl and R3 is propyl is preferred. Compositions and a method of use employing same are disclosed.

16 Claims, No Drawings

QUATERNIZED BLUE ANTHRAQINONE HAIR DYES IN AN ISATIN/AMINE DYE SYSTEM

DISCUSSION OF THE PRIOR ART

Anthraquinone compounds having a quaternary ammonium side chain and their use as hair dyes are known in the art. The prior art appreciates that there would be problems in formulating a hair dye product with dyes that have different rates of dye uptake and that positively charged dyes (i.e. basic dyes) have qualitatively different rates of dye uptake than typical neutral semipermanent dyes (i.e. direct dyes). It is also appreciated in the art that minor variations in the side chain containing the quaternary ammonium group can vary the dye uptake rate (as indicated by the color change on hair) sufficiently so that dyes with certain groups will dye at rates similar to an uncharged semipermanent dye.

Differences in rates of dye uptake can lead to another problem. Many hair dye formulations are made by a combination of yellow, red and blue dyes, in different amounts and ratios. In order to incorporate a new dye into an existing product, its rate of dyeing must be comparable to the other dyes in that particular formulation. If a hair dye product containing individual dyes which are picked up by hair at significantly different rates is applied to the hair, the shade (i.e. the color as opposed to the intensity) will change through several stages with the passing of time. For example, if the product contains blue, yellow and red dyes (with the blue dye dyeing the fastest, the yellow dye dyeing at an intermediate rate and the red dye dyeing the slowest), the hair will initially be bluish. After a certain period of time, the hair will turn greenish (blue plus yellow). Finally, when the red dye imparts its color, the hair may exhibit a brown coloration. Although this is an exaggerated case, even smaller variations would be totally unacceptable (i.e. from a bluish brown to a greenish brown). Clearly, from a consumer's point of view, a product which dyes hair in such a manner is undesirable because the consumer would never be sure of obtaining the hair color that he or she wants or even the same color from the same formulation. Obtaining the exact color is a crucial factor for a hair dye product and this is why most products offer between 25 and 50 different shades. Users frequently discover significant difficulties as much from the point of view of the formulation of hair dye mixtures as from the point of view of their application.

Patentees in U.S. Pat. No. 5,520,707 appreciate that minor changes in the quaternary ammonium side chain of a basic dye can significantly affect the rate of dye uptake.

Finally, it should be noted that U.S. Pat. No. 4,921,503 discloses a novel dyeing system using isatin or its derivatives with various amines. Color is formed in hair by reacting isatin, or its derivatives, with various amines. Due to the chemical reaction, the molecular size of the dye is increased and the color is very shampoo resistant. The system does however have a drawback. It lacks a blue isatin/amine combination. The color range is limited to yellow through violet since no amines were found that give blue coupled products. Thus it is not possible to develop a full range of shades. The most bathochromic combination described by patentees (Table 1, Col 4) has a lambda max of 528 nm. This is far from the 630 nm lambda max typical of blue semi-permanent colors, such as Disperse Blue 3. Moreover, since conventional semi-permanent dyes do not have sufficient shampoo resistance to match the properties of the isatin/amine dyeing system, there is no advantage in adding conventional blue dyes to extend the shade range of the patentees' isatin/amine system.

SUMMARY OF THE INVENTION

The present invention utilizes the anthraquinone compounds of Formula I of U.S. Pat. No. 5,520,707 in an isatin/amine dye system as disclosed in U.S. Pat. No. 4,921,503.

Anthraquinone compounds useful in the instant invention have the structures:

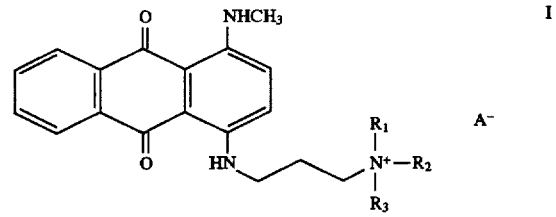

The anthraquinones of Formula I dye hair at a rate such that they can be used in formulations containing neutral semipermanent dyes. Formula I encompasses compounds Ia and Ib:

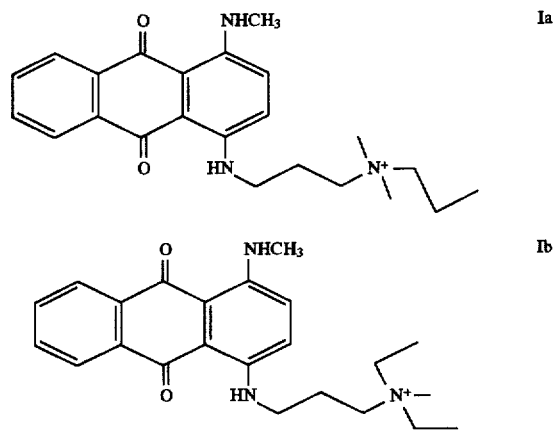

Certain quaternized blue anthraquinones, especially the compound of Formula I wherein $R_1$ and $R_2$ are methyl and $R_3$ is propyl (hereinafter referred to as Quat 1), have the required compatible shampoo resistance and, surprisingly, do not interfere with the isatin/amine color forming chemistry. Thus they can be used to extend the color range of the isatin/amine system of U.S. Pat. No. 4,921,503 allowing for formulation of a full range of shades. Quat 1 has a lambda max of 640 nm and does not interfere with the formation of the 3-arylimino-indolin-2-ones (the dyes that are produced by the reaction of isatins and amines). Importantly, unlike other semi-permanent colorants, Quat 1 has similar washfastness to the 3-arylimino-indolin-2-one dyes, making it compatible with the isatin/amine system of U.S. Pat. No. 4,921,503. Additionally, Quat 1 has a far stronger dyetake than Disperse Blue 3 (the blue dye commonly used in semi-permanent hair colorants).

It should be noted that as used throughout this specification and claims A⁻ connotes a cosmetically acceptable anion such as a halide (e.g. iodide, chloride, bromide, fluoride) an alkylsulfate (e.g. methylsulfate), or an alkylcarboxylate (e.g. acetate). Iodide is the most preferred.

The present invention comprises the use of quaternized blue anthraquinones of Formula I (as is disclosed in U.S. Pat. No. 5,520,707) in the isatin/amine dyeing system of U.S. Pat. No. 4,921,503. As stated earlier, the present inventor has discovered that certain quaternized blue anthraquinones, especially the compound of Formula I wherein $R_1$ and $R_2$ are methyl and $R_3$ is propyl (Quat 1), enable one skilled in the art to develop a full range of shades for the isatin/amine system of U.S. Pat. No. 4,921,503.

Quat 1 has a lambda max of 640 nm and surprisingly does not interfere with the formation of 3-arylimino-indolin-2-one dyes resulting from the reaction of isatins and amines.

The following Example demonstrates the advantages of using quaternized blue anthraquinones of Formula I in an isatin/amine dyeing system.

EXAMPLE

| Swatch # | Dyes[1] | Substrate[2] | Dyeout[3] | | | Washfastness[4] | |
|---|---|---|---|---|---|---|---|
| | | | L | a | b | ΔE | Δb |
| 1a | A | G | 25.53 | 6.5 | 13.70 | 4.43 | −2.00 |
| 1b | A | BL | 27.16 | 14.64 | 15.62 | 8.37 | −0.49 |
| 1c | A | WC | 43.93 | 25.18 | 27.92 | 16.20 | −0.59 |
| 2a | B | G | 15.38 | −2.50 | 3.20 | 4.76 | −0.18 |
| 2b | B | BL | 11.42 | −0.38 | 0.08 | 6.71 | −5.22 |
| 2c | B | WC | 22.31 | −3.58 | 9.40 | 13.83 | −5.48 |
| 3a | C | G | 22.13 | 1.81 | 10.61 | 6.02 | −2.21 |
| 3b | C | BL | 20.34 | 4.06 | 9.60 | 11.33 | −0.17 |
| 3c | C | WC | 26.36 | 0.35 | 11.93 | 18.19 | −7.59 |
| 4a | D | G | 19.94 | −0.90 | −8.30 | 3.93 | 2.33 |
| 4b | D | BL | 13.48 | 6.99 | −22.07 | 6.62 | −2.77 |
| 4c | D | WC | 38.27 | −0.01 | −28.13 | 11.06 | 7.37 |
| 5a | E | G | 23.73 | 0.02 | −1.24 | 6.29 | 1.31 |
| 5b | E | BL | 30.75 | −0.67 | −6.48 | 13.92 | 9.48 |
| 5c | E | WC | 34.07 | 7.07 | −29.31 | 16.53 | 10.89 |

[1] A = 1.5% isatin + 1% 4-aminophenol; B = 1.5% isatin + 1% 4-aminophenol + 1% Quat 1; C = 1.5% isatin + 1% 4-aminophenol + 1% Disperse Blue 3; D = 1% Quat 1; E = 1% Disperse Blue 3
[2] G = Blended Grey hair; BL = Commercially Bleached hair; WC = Wool cloth
[3] 1:1 Ethanol:water; 40 minutes; warm water rinse, air dry
[4] Shaken 1 hour in 10% Logics Clarifying Shampoo It should be noted that "L" represents the intensity of the color and "a and b" represent the relative purity of the color with "a" being the relative greenness or redness of the color and "b" being the relative yellowness or blueness of the color. ΔE is the total color difference and is defined by the equation:

$$\Delta E = \sqrt{(\Delta L)^2 + (\Delta a)^2 + (\Delta b)^2}$$

Δ's (e.g. ΔL, Δa, Δb) refer to the change in that parameter for some operation

Obviously, Quat 1 gives a stronger and bluer dyeout both alone (swatches 4 vs. swatches 5, L values and b values, respectively) and in the isatin-amine system (swatches 2 vs. swatches 3, again L and b). [It should be noted that the lower the L value the more intense the color and the lower the b value (including into negative numbers) the more blue the color].

Most importantly, the washfastness of Quat 1 is superior to DB 3 (ΔE's and Δb's, swatches 4 vs. 5) and more similar to that of the isatin-amine dyes (ΔE's of swatches 1 and 2 vs. swatches 1 and 3). Thus Quat 1 is clearly an important addition to the isatin-amine dyeing system of U.S. Pat. No. 4,921,503. This utility is surprising since Quat 1 is structurally very similar to Disperse Blue 3.

The present invention also encompasses an improvement to hair dye compositions containing isatin or an isatin derivative with an amine. The improvement comprises the composition also contains a quaternized blue anthraquinone of Formula I. Preferably the quaternized blue anthraquinone of Formula I is Quat 1.

Dye compositions employing the anthraquinone/isatin amine dye system of the present invention may be formulated as a solution, a liquid shampoo (which can be a solution or an emulsion), a cream, a gel, a powder or an aerosol.

Materials typically included in hair dye compositions and/or developers include for example, organic solvents and solubilizing agents, surface active agents, thickening agents, buffers, chelating agents, perfumes, sunscreens, conditioners, dyeing assistants or penetrating agents, preservatives, emulsifiers and fragrances. A particular material may perform several functions. For example, a surfactant may also act as a thickener. The dye compounds of Formula I are cationic. The dye uptake of cationic dyes is inhibited by an excess of certain anionic materials with which the cationic dyes would complex, precipitate or similarly react. Consequently, care should be exercised in formulating with such materials.

It is often advantageous to include in the dye compositions of the present invention an organic solvent or solvent system which helps solubilize the dyes and adjuvants contained in the compositions. A number of organic solvents are known for such purpose. These include: alcohols, particularly alkyl alcohols of 1–6 carbons, especially ethanol and propanol; glycols of up to about 10 carbons, preferably less than 6 carbons, especially propylene glycol and butylene glycol; glycol ethers of up to about 10 carbons, especially diethyleneglycol monobutyl ether; carbitols; and benzyl alcohol. When present, the solvents will constitute from about 1% to about 60%, preferably from about 10 to about 30%, by weight of the dyeing composition.

Typical surfactant types useful in the compositions of the invention include: alkyl sulfates, alkyl ether sulfates, amide ether sulfates, soaps, alkyl ether carboxylates, acylsarcosinates, protein/fatty acid condensates, sulfosuccinic acid esters, alkane sulfonates, alkylbenzene sulfonates, alpha-olefin sulfonates, acylisethionates, acyltaurines, ethoxylates, sorbitan esters, alkanolamides, amnine oxides, quaternary ammonium salts, alkyl betaines, amidopropyl betaines, sulfobetaines, glycinates/aminopropionates and carboxyglycinates/amino-dipropionates. A combination of different surfactants can be used to impart particular viscosity and foaming properties.

Illustrative of specific surfactants that may be employed are: lauryl sulfate; polyoxyethylene lauryl ester; myristyl sulfate; glyceryl monostearate; sodium salt of palmitic acid, methyl taurine; cetyl pyridinium chloride; lauryl sulfonate; myristyl sulfonate; lauric diethanolamide; polyoxyethylene stearate; stearyl dimethyl benzyl ammonium chloride; dodecyl benzene sodium sulfonate; nonyl naphthalene sodium sulfonate; dioctyl sodium sulfosuccinate; sodium N-methyl-N-oleyl taurate; oleic acid ester of sodium isethionate; sodium dodecyl sulfate, and the like. The quantity of water soluble surface active agent employed can vary widely up to about 15%. Preferably, the surface active agent is employed in an amount of from about 0.10% to about 10%, based on the weight of the composition. Note however that when an anionic surfactant is employed the amount must be restricted so as to avoid possible incompatibility with the dye compounds of the present invention.

The thickening agent, when employed, may be one or a mixture of those commonly used in hair dyeing compositions or in hair developers. Such thickening agents include: sodium alginate; gum arabic; cellulose derivatives, such as methylcellulose or the sodium salt of carboxymethylcellulose; acrylic polymers, such as polyacrylic acid sodium salt; and inorganic thickeners, e.g., bentonite and fumed silica. Electrolytes, alkanolamides, cellulose ethers and highly ethoxylated compounds (such as ethers, esters and diesters)

may also be used to thicken the composition. The quantity of thickening agent can vary over a wide range. Typically the thickening agent(s) is employed in an amount of up to about 20%, more preferably, from about 0.1% to 5%, based on the weight of the composition.

The pH of the dye composition can vary from about 2.5 to about 11. Any compatible water-dispersible or water soluble alkalizing agent can be incorporated in the composition in an amount suitable to give the desired pH. Typically, the amount of alkalizing agent employed is less than about 10%, preferably, from about 0.1% to about 5%, based on the weight of the composition.

Compatible alkalizing agents are those which under the conditions of use do not interact chemically with the dye(s) employed, that do not precipitate the dye(s), and are non-toxic and non-injurious to the scalp. Preferred alkalizing agents include: mono-, di- and trialkanolamines, such as triethanolamine and 2-amino-2-methyl-1,3-propanediol; alkyl amines, such as monoethylamine, diethylamine and dipropylamine; and heterocyclic amines, such as morpholine, piperidine, 2-picoline and piperazine.

Any inorganic or organic acid or acid salt, that is compatible with the dye composition and does not introduce toxicity under its conditions of use, can also be employed to adjust the pH of the dye composition. Illustrative of such acids and acid salts are sulfuric acid, formic acid, acetic acid, lactic acid, citric acid, tartaric acid, ammonium sulfate, sodium dihydrogen phosphate, and potassium bisulfate.

Common chelating agents that can be employed in the compositions of the invention include the salts of ethylenediaminetetraacetic acid (EDTA), nitrilotriacetic acid, phosphates, pyrophosphates and zeolites.

Conditioners that can be incorporated in the present compositions include: encapsulated silicones; silicones, such as amino-functional and carboxy silicones; volatile silicones; combinations of a cationic polymer, a decomposition derivative of keratin and a salt; quaternary ammonium compounds such as cocoa — $(C_{12-18})$-alkyl poly (6) oxyethyl di-(2-lauroyloxyethyl)-methyl ammonium chloride; combinations of a plant extract and a polypeptide; a dimethyl diallyl ammonium chloride (DMDAAC)/acrylic acid type polymer; and a dialkyl quaternary ammonium compound where the alkyl groups are $C_{12}$–$C_{16}$. Other well known conditioners, such as lanolin, glycerol, oleyl alcohol, cetyl alcohol, mineral oil and petrolatum, can also be incorporated.

It is a common practice to add solvents or swelling agents to enhance the penetration of hair dyes. Materials useful for swelling hair include acetic acid, formic acid, formamide, urea, ethyl amine and certain alkali halides (potassium iodide, sodium bromide, lithium bromide and lithium chloride, but not sodium chloride). N-Alkyl pyrrolidones and epoxy pyrrolidone may be employed to potentially increase the penetration of dye into hair. Imidazolines, such as disclosed in U.S. Pat. No. 5,030,629, may be employed in the compositions to enhance the penetration of hair dyes.

Emulsifiers may be used when the final form of the hair dye is an emulsion. By their nature, many emulsifiers are also surfactants. There are five general categories: anionic, cationic, nonionic, fatty acid esters and sorbitan fatty acid esters. Examples include: mono-, dialkyl and trialkyl ether phosphates, long-chain fatty acids with hydrophilic compounds such as glycerin, polyglycerin or sorbitol and long chain alkyl primary and secondary amines, quaternary ammonium and quaternary pyridinium compounds.

Materials which may render the product aesthetically more appealing, such as fragrances, proteins hydrolysates, vitamins and plant extracts, may be added. Examples include chamomile, aloe vera, ginseng, and pro-vitamin B.

What is claimed is:

1. In a method for dyeing a keratin fiber by contacting the fiber with a tinctorially effective amount of isatin or isatin derivative/amine reaction product, the improvement which comprises the fiber is also contacted with a tinctorially effective amount of a quaternized blue anthraquinone compound of Formula I

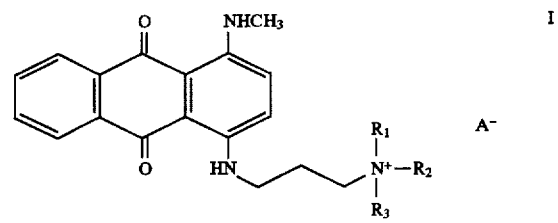

wherein $R_1$ and $R_2$ are methyl and $R_3$ is propyl, or $R_1$ and $R_2$ are ethyl and $R_3$ is methyl, and $A^-$ is a cosmetically acceptable anion.

2. The method as claimed in claim 1, wherein $R_1$ and $R_2$ are methyl and $R_3$ is propyl.

3. The method as claimed in claim 1, wherein $R_1$ and $R_2$ are ethyl and $R_3$ is methyl.

4. The method as claimed in claim 1, wherein the anion is selected from the group consisting of iodide, chloride, bromide, fluoride, methylsulfate, and acetate.

5. A composition for dyeing a keratin fiber comprising a tinctorially effective amount of an isatin or isatin derivative/amine reaction product; a tinctorially effective amount of a quaternized blue anthraquinone compound of formula I

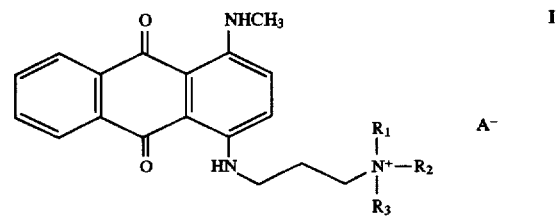

wherein $R_1$ and $R_2$ are methyl and $R_3$ is propyl, or $R_1$ and $R_2$ are ethyl and $R_3$ is methyl, and $A^-$ is a cosmetically acceptable anion; and a cosmetically acceptable vehicle.

6. The composition, as claimed in claim 5, wherein in the anthraquinone of Formula I $R_1$ and $R_2$ are methyl and $R_3$ is propyl.

7. The composition, as claimed in claim 5, wherein in the anthraquinone of Formula I $R_1$ and $R_2$ are ethyl and $R_3$ is methyl.

8. The composition, as claimed in claim 5, wherein the anion is selected from the group consisting of iodide, chloride, bromide, fluoride, methylsulfate, and acetate.

9. A method for dyeing a hair fiber on a living human head comprising contacting said fiber with a tinctorially effective amount of an isatin or isatin derivative/amine reaction product and a tinctorially effective amount of a quaternized blue anthraquinone compound of Formula I

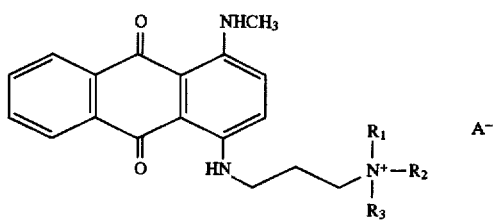

wherein $R_1$ and $R_2$ are methyl and $R_3$ is propyl, or $R_1$ and $R_2$ are ethyl and $R_3$ is methyl, and $A^-$ is a cosmetically acceptable anion, in a cosmetically acceptable vehicle;

said contacting being for a time sufficient to dye said fiber.

10. The method, as claimed in claim 9, wherein in the anthraquinone compound of Formula I, $R_1$ and $R_2$ are methyl and $R_3$ is propyl.

11. The method, as claimed in claim 9, wherein in the anthraquinone compound of Formula I, $R_1$ and $R_2$ are ethyl and $R_3$ is methyl.

12. The method, as claimed in claim 9, wherein the anion is selected from the group consisting of iodide, chloride, bromide, fluoride, methylsulfate, and acetate.

13. The method, as claimed in claim 1, wherein the contacting is simultaneous.

14. The method, as claimed in claim 1, wherein the contacting is sequential.

15. The method, as claimed in claim 9, wherein the contacting is simultaneous.

16. The method, as claimed in claim 9, wherein the contacting is sequential.

* * * * *

UNITED STATES PATENT AND TRADEMARK OFFICE
CERTIFICATE OF CORRECTION

PATENT NO. : 5,746,779
DATED      : May 5, 1998
INVENTOR(S) : Keith Brown

It is certified that error appears in the above-identified patent and that said Letters Patent is hereby corrected as shown below:

On the title page: Item [54] and Column 1, line 1, "Anthraqinone" should read -- Anthraquinone --.

Signed and Sealed this

Twenty-first Day of September, 1999

*Attest:*

*Attesting Officer*

Q. TODD DICKINSON

*Acting Commissioner of Patents and Trademarks*